United States Patent [19]

Reierson et al.

[11] Patent Number: 4,659,861
[45] Date of Patent: Apr. 21, 1987

[54] NOVEL NITRILE FUNCTIONAL GLYCOL ETHER ACETALS

[75] Inventors: Robert L. Reierson; Gary P. Rabold, both of Midland, Mich.

[73] Assignee: The Dow Chemical Company, Midland, Mich.

[21] Appl. No.: 317,801

[22] Filed: Nov. 3, 1981

[51] Int. Cl.[4] .................. C07C 121/16; C07C 121/66; C07C 121/75; C07C 121/28

[52] U.S. Cl. .................................. 558/448; 558/410; 558/441; 252/77

[58] Field of Search .............. 260/465.6, 465 F, 465.4; 558/410, 441, 448

[56] References Cited

U.S. PATENT DOCUMENTS

| | | | |
|---|---|---|---|
| 2,370,663 | 3/1945 | Hill | 252/77 |
| 2,386,736 | 10/1945 | Bruson | 260/465.4 X |
| 2,404,164 | 7/1946 | Carpenter | 260/692 X |
| 2,447,975 | 8/1948 | Croxall | 252/73 X |
| 2,809,988 | 10/1957 | Heininger | 260/465.6 |
| 2,836,613 | 5/1958 | Heininger | 260/465.6 |
| 3,138,616 | 6/1964 | Scotti et al. | 260/464 X |
| 3,150,142 | 9/1964 | Eby | 564/189 X |
| 3,513,185 | 5/1970 | Cresswell et al. | 260/465.6 X |
| 3,538,003 | 11/1970 | Lothar | 252/77 |
| 3,563,893 | 2/1971 | Doelling et al. | 252/74 X |
| 3,658,904 | 4/1972 | Kuper | 585/863 X |
| 3,671,564 | 6/1972 | Cresswell et al. | 260/465.6 X |
| 3,779,930 | 12/1973 | Alcorn | 252/79 X |
| 4,058,469 | 11/1977 | Hoke | 252/51.5 |
| 4,320,024 | 3/1982 | Reierson et al. | 252/78.3 |
| 4,365,073 | 12/1982 | Bremmer et al. | 549/451 |

Primary Examiner—Joseph Paul Brust
Attorney, Agent, or Firm—D. N. Deline

[57] ABSTRACT

Novel nitrile functional glycol ether acetals that are useful components of hydraulic pressure transmission fluids are described.

6 Claims, No Drawings

NOVEL NITRILE FUNCTIONAL GLYCOL ETHER ACETALS

BACKGROUND OF THE INVENTION

In U.S. Pat. No. 3,658,904, certain 3-cyano acetals prepared by reacting $C_{1-30}$ alcohols with acrylonitrile or $\alpha$-alkyl derivatives thereof were described. The compounds were useful as solvents for the selective extraction and separation of hydrocarbons.

In U.S. Pat. No. 3,138,616, similar acetals were prepared by reaction of monohydric alcohols with $\beta$-cyanoacetaldehyde. The compounds were intermediates for preparation of textile conditioners and pharmaceuticals.

In U.S. Pat. No. 3,563,893, non-nitrile functional glycol ether acetals were described. The compounds were found to be suitable hydraulic fluid components. Hydraulic fluid formulations containing such compounds have been limited due to excessive rubber swelling, thereby necessitating the use of excessive amounts of rubber shrinking agents to ultimately arrive at a fluid having acceptable rubber compatibility. For example, polyethylene glycols may be added to the fluid formulation. However, the physical properties of the resulting fluids oftentimes is impaired by such additives.

SUMMARY OF THE INVENTION

According to the invention certain novel nitrile functional glycol ether acetals are described having the formula:

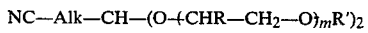

NC—Alk—CH—(O—(CHR—CH$_2$—O)$_m$R')$_2$ where Alk is a divalent $C_{2-10}$ moiety selected from the group consisting of alkylene and aryl, cyano, alkoxy and alkoxycarbonyl substituted derivatives thereof; R independently each occurrence is hydrogen, methyl or ethyl; R' is lower alkyl; and m independently each occurrence is an integer from zero to about 20 provided that in at least one occurrence m is greater than or equal to 1.

The compounds have been found to be particularly suitable for use in functional fluids such as hydraulic fluids and heat transfer fluids. In particular, certain of the compounds have been found to possess both good rubber compatibility and relatively high wet boiling points. Additionally, because Alk of the above formula contains at least two carbons, the compounds are more stable than the corresponding methylene-containing nitrile functional acetals which under basic conditions may form vinyl ether derivatives.

Suitable hydraulic fluids containing the invented compounds may easily be formulated employing known hydraulic fluid components and additives in addition to one or more of the invented compounds.

DETAILED DESCRIPTION OF THE INVENTION

The novel nitrile functional glycol ether acetals of the invention may be prepared by the transacetalization reaction of the nitrile functionalized methyl acetals of the formula:

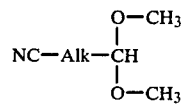

where Alk is as previously defined; with one or more lower alkyl monoethers of (poly)alkylene glycols having the formula

HO(CHRCH$_2$O)$_m$R' where R, R' and m are as previously defined.

The reaction is conducted at temperatures from about 0° C. to about 200° C. and preferably from about 20° C. to 100° C. Methanol, the by-product formed by the reaction, may easily be removed by distillation preferably at reduced pressure. The reaction takes place upon contacting of the reactants in the presence of a strong acid. Typically, they are contacted by stirring at the desired temperature. Ordinary glass or metal reactors which are unreactive with the reactants may be suitably employed. Suitable strong acids include sulfuric acid, methane sulfonic acid, toluene sulfonic acid, heterogeneous strongly acidic ion-exchangers, and the like.

Suitable nitrile functionalized methyl acetal reactants may be purchased commercially or prepared according to the technique of U.S. Pat. No. 3,658,904 which teaching is incorporated herein by reference. Alternatively they may be prepared by reaction of the corresponding nitrile functionalized aldehyde with methanol. Alternatively, where the corresponding nitrile functionalized aldehyde is available, the invented compounds may be prepared directly by reaction with the desired (poly)alkylene glycol ether or mixture thereof.

Preferred nitrile functional glycol ether acetals are those wherein Alk is ethylene, e.g., those compounds prepared from 4,4-dimethoxybutane nitrile, NC—CH$_2$CH$_2$CH(OCH$_3$)$_2$. Highly preferred are those acetals containing primary ether groups, e.g., reaction products of 4,4-dimethoxybutane nitrile with monoalkyl ethers of (poly)ethylene glycol. Therefore, these compounds are of the formula NC—CH$_2$CH$_2$—CH—(O—(CH$_2$CH$_2$O )$_m$R')$_2$. Most preferred are such compounds having up to about three ethyleneoxy repeating units in the ether chain, e.g., those compounds wherein m and n are less than or equal to three.

In the use of the invented compounds in hydraulic fluid formulations, numerous hydraulic fluid components and additives may be combined with the present compounds in order to prepare a fluid having the desired properties of viscosity, boiling points, elastomer and water compatibility, etc. One or more of the invented compounds may be present in the hydraulic fluid in major or minor proportions.

Components of hydraulic fluids with which the invented compounds may suitably be combined include conventional hydraulic fluid components such as the well-known (poly)alkylene glycols and monoalkyl ethers, esters and orthoesters thereof. Also suitably employed are borate esters formed by esterification of one or more moles of a (poly)alkylene glycol, a monoalkyl ether derivative of a (poly)alkylene glycol or a mixture thereof, with one or more moles of boric acid or similar borate ester-forming precursor.

Also included in the list of suitable components for combination with the invented compounds to prepare a hydraulic fluid are certain novel nitrile functional cyclic ketals and acetals described in copending application Ser. No. 159,332, filed June 16, 1980, in the name of Robert L. Reierson et al., now U.S. Pat. No. 4,320,074.

In addition to such components which may be combined with the invented compounds in a hydraulic fluid formulation, various additives may be employed to impart desirable qualities to the fluid. Included are such additives as lubricants, fire retardants, antioxidants, corrosion inhibitors, pour point depressants, dyes, odor suppressants, etc., which are previously known in the art.

SPECIFIC EMBODIMENTS

The following examples are presented as illustrative of the present invention and the present invention should not be construed as limited thereto.

EXAMPLE 1—4-methoxy-4-(2-(2-methoxyethoxy)ethoxy)butane nitrile and 4,4-di(2-(2-methoxyethoxy)ethoxy)butane nitrile In a glass reaction flask, 4,4-dimethoxybutane nitrile (347 g, 2.7 moles), 2-(2-methoxyethoxy)ethanol (300 g, 2.5 moles) and anhydrous methane sulfonic acid (1.31 g, 0.014 mole) were combined at room temperature, stirred for 15 minutes and then subjected to vacuum to remove methanol formed by the reaction. A second quantity of 4,4-dimethoxybutane nitrile (124 g, 0.96 mole) was added and the vacuum stripping continued with heating to 40° C.-50° C. The solution was neutralized with triethylamine and vacuum distilled at 0.1 Torr. The fractions boiling at 89° C.-106° C., 183 g, and at 168° C.-170° C., 121 g, were identified as 4-methoxy-4-(2-(2-methoxyethoxy)ethoxy)butane nitrile and 4,4-di(2-(2-methoxyethoxy)ethoxy)butane nitrile, respectively, by standard techniques of nuclear magnetic resonance and infrared spectroscopy and mass spectrometry.

EXAMPLE 2—4,4-di(2-methoxyethoxy)butane nitrile

The reaction procedure of Example 1 was substantially repeated except that the glycol ether reactant employed was 2-methoxyethanol. Vacuum distillation as in Example 1 resulted in a mixture of mono- and diglycol ether reaction products. 4,4-Di(2-methoxyethoxy)butane nitrile (b.p. 89° C.-91° C., 0.1 Torr) was isolated in high purity by further distillation.

EXAMPLE 3—4,4-di(2-methoxy-1-methylethoxy)butane nitrile

The reaction conditions of Example 1 were again substantially repeated except that the glycol ether reactant employed was 1-methyl-2-methoxyethanol (50 percent molar excess based on stoichiometry). The reaction mixture was flash distilled to provide a mixture of reaction products, principally 4-methoxy-4-(1-methyl-2-methoxyethoxy)butane nitrile.

EXAMPLE 4—Properties

The compounds prepared in Examples 1 and 2 were tested for suitable properties for use in a hydraulic fluid including wet equilibrium reflux boiling point (ERBP), viscosity at −40° F., and rubber compatibility. The tests were performed in accordance with procedures established by the Federal Motor Vehicle Safety Standard, 49 CFR §571.116 (1976). Results of the tests and comparative results with other known compounds are presented in Table I. Due to limited availability of some of the novel compounds not all tests could be performed.

TABLE I

| Run | Compound | (wet) ERBP °F. (°C.) | % H$_2$O absorbed | Viscosity 40° F. (Cst) Dry | Viscosity 40° F. (Cst) Wet | Rubber Cup swelling (in) | Rubber Cup Hardness (IRHD) |
|---|---|---|---|---|---|---|---|
| 1 | NC(CH$_2$)$_2$CH(OCH$_2$CH$_2$OCH$_3$)$_2$ (Example 2) | 325 (163) | 1.96 | 785 | 804 | 0.042 | −8 |
| 2 | NC(CH$_2$)$_2$—CH(OCH$_3$) \| O—(CH$_2$CH$_2$O)$_2$—CH$_3$ (Example 1) | 334 (168) | 2.04 | 895 | — | 0.031 | −9 |
| 3 | NC(CH$_2$)$_2$CH(O(CH$_2$CH$_2$O)$_2$CH$_3$)$_2$ (Example 1) | 326 (163) | 2.05 | 3124 | — | — | — |
| 4 | DOT-3 | 284 (140) (min) | — | 1500 (max) | 1500 (max) | 0.006 to 0.055 | 0 to −15 |
| 5 | DOT-4 | 311 (155) (min) | — | 1800 (max) | 1800 (max) | 0.006 to 0.055 | 0 to −15 |
| 6[a] | NC(CH$_2$)$_2$CH(OCH$_3$)$_2$ | 307 (153) | 1.74 | 60 | fail[b] | 0.065 | −12 |
| 7[a] | NC(CH$_2$)$_2$CH(OCH$_3$)$_2$[c] | 326 (163) | 1.72 | — | — | — | — |
| 8[a] | NC(CH$_2$)$_2$CH(OC$_2$H$_5$)$_2$ | 314 (157) | 1.33 | 68 | fail[b] | — | — |
| 9[a] | CH$_2$(OCH$_2$CH$_2$OCH$_2$CH$_2$OCH$_3$)$_2$ | 304 (151) | 2.31 | 87 | 121 | 0.137 | −15 |

[a]Comparative example.
[b]Severe ice crystal formation.
[c]Second sample.

The test results indicate that the invented compounds are well suited for use in hydraulic fluids and in general meet or may be compounded to meet the standards of a DOT-4 hydraulic brake fluid. The excessive viscosity of the invented compound of Run 3 may be easily compensated by the use of less viscous hydraulic fluid components of Runs 1 or 2. By contrast the prior art compounds of Runs 6, 7, 8 and 9 possessed inferior properties of wet equilibrium reflux boiling point, rubber compatibility or water compatibility at reduced temperatures, e.g., ice formation.

What is claimed is:

1. A compound of the formula:

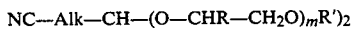

NC—Alk—CH—(O—CHR—CH$_2$O)$_m$R')$_2$ where Alk is a divalent C$_{2-10}$ moiety selected from the group consisting of alkylene and aryl, cyano, alkoxy and alkoxycarbonyl substituted derivatives thereof; R independently each occurrence is hydrogen, methyl, or ethyl; R' is lower alkyl; and m independently each occurrence is an integer from zero to about 20 provided that in at least one occurrence m is greater than or equal to 1.

2. A compound according to claim 1 wherein Alk is ethylene.

3. A compound according to claim 2 that is 4,4-di(2-methoxy-1-methylethoxy)butane nitrile.

4. A compound according to claim 2 of the formula

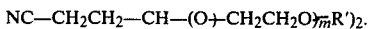

5. A compound according to claim 4 wherein m is less than or equal to three.

6. A compound according to claim 5 that is 4-methoxy-4-(2-(2-methoxyethoxy)ethoxy)butane nitrile, 4,4-di(2-(2-methoxyethoxy)ethoxy)butane nitrile, or 4,4-di(2-methoxyethoxy)butane nitrile.

* * * * *